United States Patent [19]

Borovsky

[11] Patent Number: 5,144,144
[45] Date of Patent: Sep. 1, 1992

[54] CONTACT LENS CLEANING AND DISINFECTING SYSTEM

[75] Inventor: Simcha Borovsky, Fair Lawn, N.J.
[73] Assignee: American Vision, Inc., Glen Rock, N.J.
[21] Appl. No.: 732,623
[22] Filed: Jul. 19, 1991
[51] Int. Cl.[5] .................. H01J 37/20; G01N 23/00
[52] U.S. Cl. ................... 250/455.11; 422/24
[58] Field of Search .................. 250/455.1; 422/24

[56] References Cited

U.S. PATENT DOCUMENTS

| | | | |
|---|---|---|---|
| 3,433,949 | 3/1969 | TruhaM | 250/455.1 |
| 3,852,032 | 12/1974 | Urbach | 250/455.1 |
| 4,063,890 | 12/1977 | Baron | 250/455.1 |
| 4,448,750 | 5/1984 | Fuesting . | |
| 4,698,206 | 10/1987 | Nevin . | |
| 4,735,209 | 4/1988 | Foody . | |
| 4,752,444 | 6/1988 | Bowen et al. . | |
| 4,755,292 | 7/1988 | Merriam . | |
| 4,772,795 | 9/1988 | Sakural et al. . | |
| 4,868,397 | 9/1989 | Tittel . | |
| 4,882,496 | 11/1989 | Bellotti et al. . | |
| 4,899,057 | 2/1990 | Koji | 250/455.1 |
| 4,952,812 | 8/1990 | Miripol et al. . | |
| 5,017,790 | 5/1991 | Kojima | 250/455.1 |

Primary Examiner—Bruce C. Anderson
Attorney, Agent, or Firm—Leighton K. Chong

[57] ABSTRACT

A contact lens cleaning and disinfecting system is formed as a compact unit with an upper housing portion containing a UV lamp and a lower base portion containing a cleaning/disinfecting chamber which is filled with saline solution, a lens holder, a turbulence mechanism for inducing turbulence in the fluid, and an electronic control unit for operating the UV lamp and the turbulence mechanism in a single cleaning/disinfecting cycle of comparatively short duration. The lens holder has a pair of lower lens holder portions for the lenses and an upper bracket for shading the lenses from direct UV radiation. The turbulence mechanism is a magnetic pedal, tethered on the end of a flexible spring, which is driven by a magnetic flux generator to create a whirlpool in the fluid which swirls in and around the lens holder portion. Particles, films, and other deposits dislodged from the lenses are carried by the whirlpool above the upper bracket of the lens holder where they are disinfected by the UV radiation. The pedal is driven in oscillation in a sub-sonic range of about 50–120 cyc/-sec. An electrical contact interlock between the upper housing and the lower base prevents accidental operation and irradiation by the UV lamp. The whirlpool turbulence cleans deposits from the lenses, thereby avoiding the need for manual scrubbing and detergent chemicals. The UV radiation disinfects the dislodged deposits and fluid quickly, without heating, and without the need for preservatives and disinfectant chemicals.

20 Claims, 5 Drawing Sheets

CONTACT LENS CLEANING AND DISINFECTING SYSTEM

FIELD OF THE INVENTION

This invention generally relates to a contact lens care system, and particularly to one which has provision for cleaning and disinfection of the lenses in one integrated unit.

BACKGROUND ART

Contact lenses have become widely used, and advanced lens materials and care products have been introduced in recent years. However proper care still remains an expensive and time consuming process which tends to discourage potential users or causes users not to follow the recommended care procedures. Proper contact lens care should include removing foreign particles, smoke film, and other deposits such as mucous, proteins, and enzymes from the lenses and disinfection of organisms in the deposits and the lenses to prevent causing eye infections from their subsequent use. Disinfection is particularly important for the use of "soft" (hydrophilic) contact lenses which will adsorb moisture from the cleaning solution.

The conventional cleaning process includes a daily regime of scrubbing (by manual rubbing) the lenses manually with soap or a detergent, then rinsing off in water. The use of tap water is not recommended due to the presence of hard minerals in most tap water. Besides being inconvenient, the manual rubbing and handling of the lenses during cleaning can cause scratches or microscopic damage to the lenses. The lenses must then be disinfected, by soaking the lenses in a chemical solution and/or by heating for as long as six hours or overnight. The disinfection cycle is long, and the soaking solution usually contains detergents, enzyme removers, preservatives, and other chemicals which can be adsorbed into the lenses and become very irritating to the eyes and membranes. Heat disinfection is not effective for cleaning deposits from the lenses, but rather tend to bake mineral deposits onto the lens surface. Also, repeated heating of the lenses for the disinfection cycle eventually causes physical degradation of the lens material.

Some systems have been designed for disinfection of contact lenses by ultraviolet radiation to kill microorganisms, for example, as disclosed in U.S. Pat. No. 4,063,890 to N. Baron and U.S. Pat. No. 4,868,397 to P. Tittel. However, the ultraviolet radiation poses a risk of UV degradation of the lens polymer material after repeated disinfection cycles. Also, prior manual cleaning is still required, which is inconvenient and risks damage to the lenses.

SUMMARY OF THE INVENTION

It is therefore a principal purpose of the invention to provide a system which cleans deposits from and disinfects the contact lenses conveniently and in a relatively short time. It is a particular object to develop a system which does not utilize irritating chemicals, preservatives, detergents, or enzyme removers, and which can disinfect the lenses without heating or the use of disinfectant chemical solutions.

In accordance with the present invention, a contact lens cleaning system comprises: an enclosed housing having a chamber for holding a volume of fluid therein; a source of ultraviolet radiation mounted at an upper portion of the chamber above the volume of fluid; a lens holder for holding contact lenses in the chamber immersed in the volume of fluid; a turbulence mechanism for inducing turbulence in the volume of fluid with sufficient force to dislodge particles, films, and other deposits from the lenses into the fluid; and an electronic control unit for operating the source of ultraviolet radiation to disinfect the dislodged particles, films, and other deposits in the fluid.

In the preferred embodiment, the lens holder has a pair of lower lens holder portions carried by an upper bracket having a pair of arms which are mounted onto respective sides of the housing to suspend the lens holder portions in the fluid. The upper bracket portion is immersed in the fluid interposed between the UV source and the lens holder portions to prevent UV rays from directly irradiating on the contact lenses, thereby preventing UV degradation of the lens polymer material.

The turbulence mechanism is in the form of a magnetic pedal or rotor which is positioned at a central position on a bottom portion of the chamber and is driven by a magnetic flux generator in order to generate a whirlpool which swirls in and around the lens holder portions. Particles, films, and other deposits dislodged from the lenses are carried by the whirlpool to an upper part of the fluid volume above the upper bracket of the lens holder where they are disinfected by the UV radiation. The disinfected deposits tend to settle on the upper bracket where they are collected and later removed.

The housing is preferably formed with a lower base portion containing the cleaning and disinfecting chamber, turbulence mechanism, and electrical controls for the system. The UV source is a germicidal UV lamp mounted in an upper housing portion which is fitted onto the lower base portion during use. The upper portion has electrical contacts for the UV lamp which are placed in electrical contact with corresponding contacts in the base portion during use. This construction ensures that power can be supplied to the UV lamp only when the upper portion is fitted onto the base portion, thereby precluding any harm to the user from accidental UV irradiation. A monitoring circuit monitors the operation of the UV lamp and the turbulence mechanism and provides a visual indication via an LED.

The whirlpool turbulence generates sufficient fluid force to dislodge deposits from the lenses, thereby avoiding the need for manual rubbing and detergent chemicals entirely. The UV radiation disinfects the dislodged deposits and fluid quickly, without heating, and without the need for preservatives and disinfectant chemicals. The cleaning fluid is a simple (non-preserved) saline solution which will not cause irritation to the eye.

The cleaning is accomplished in a single cycle in the cleaning unit without external intervention. The total cleaning cycle can be as short as 30 minutes. The system is designed as a self-contained electronically-controlled unit which operates on low voltage (14 volts) stepped down by a wall-plugged transformer from standard line voltage. The system does not generate any excessive heat, use toxic or irritant chemicals, or risk hazardous radiation.

Other objects, features and advantages of the present invention will be apparent from the following detailed description of the preferred embodiments with reference to the drawings, of which:

DETAILED DESCRIPTION OF THE INVENTION

Figure 1:
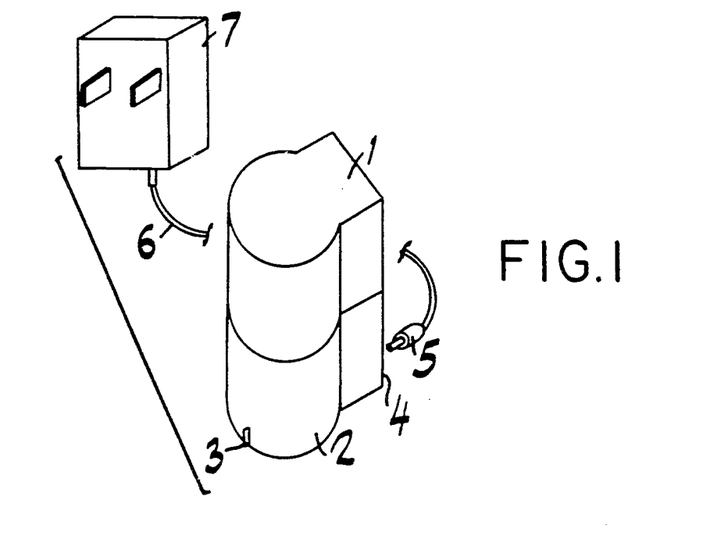
FIG. 1 is an external perspective view of a contact lens cleaning system in accordance with the present invention.

Referring to FIG. 1, a preferred embodiment of the contact lens cleaning system of the present invention has an upper housing portion 1, which contains a germicidal ultraviolet (UV) lamp, and a lower base portion which accomodates a cleaning and disinfecting chamber and electronic control circuit for the system. An indicator light 3 is provided to indicate the operation of the unit during a cleaning cycle. Low voltage (14 volts) is supplied to the unit through a receptacle connector 4 which is coupled to a low voltage plug end 5 of a power cord 6 from a step-down power transformer unit 7. The transformer unit 7 is typically an isolation, UL-approved, wall-plugged transformer which can be selected to be operated on 120 or 220 volt line supply.

Figure 2:
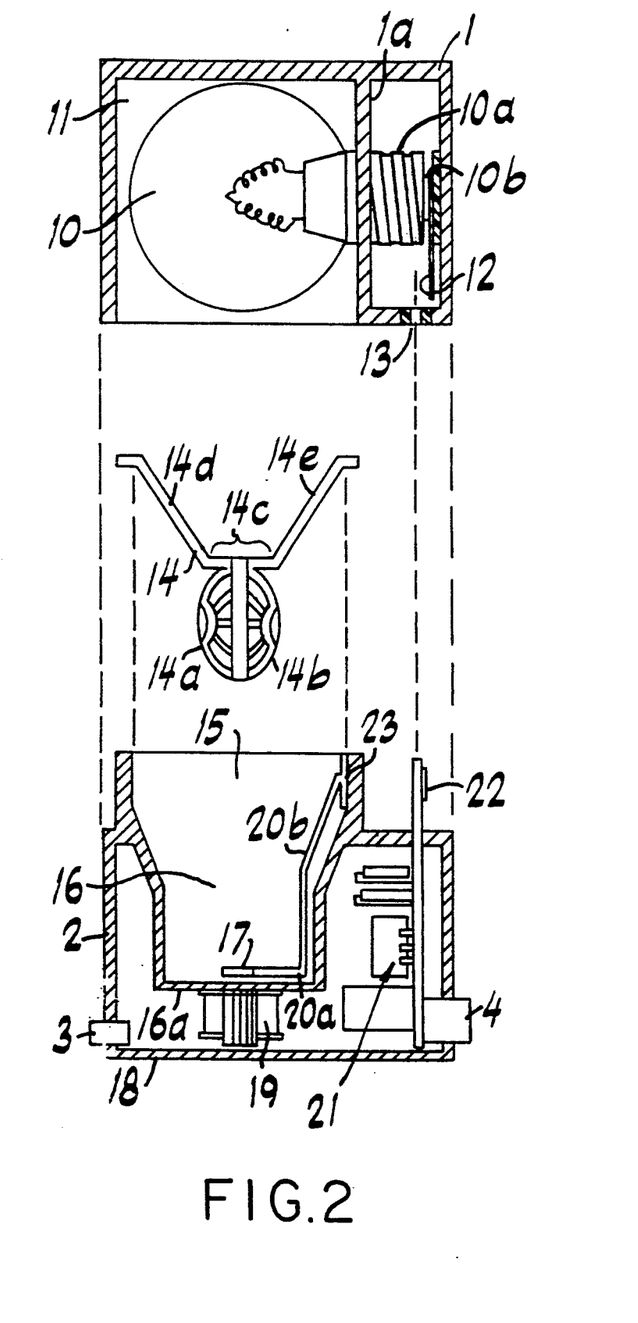
FIG. 2 is a side sectional view of the contact lens cleaning system with a cover portion, lens holder, and lower base portion.

In FIG. 2, the components of the contact lens cleaning system is shown in greater detail. The ultraviolet lamp 10 is mounted in the upper housing portion 1 with its head positioned in a cavity 11 which serves as a partial reflector for UV light generated by the lamp. The base 10a of the lamp is held in a mounting partition 1a which is grounded with the unit's chassis, and a center contact 10b is placed in electrical contact with a metal contact element 12. Access to the contact element 12 is provided through a port opening 13 in the upper housing portion 1.

Figure 4:
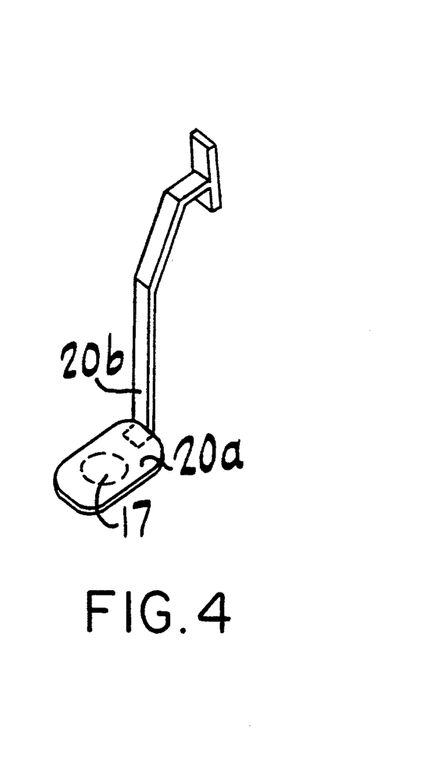
FIG. 4 is a detailed view of a magnetic pedal used to generate fluid turbulence in the cleaning system.

The lower base portion 2 is formed with a base housing wall 18, a chamber having an upper disinfecting portion 15 and a lower cleaning portion 16, and a turbulence-inducing mechanism in the form of a permanent disk magnet 17 encapsulated inside a plastic pedal 20a on the end of a flexible stainless steel spring 20b (see FIG. 4). A driving transformer 19 is located below a bottom wall 16a of the cleaning chamber, for generating a fluctuating magnetic flux which drives the magnetic pedal 20a into oscillation. When cleaning fluid is filled in the cleaning and disinfecting chamber 15-16, the oscillation of the magnetic pedal 20a creates a whirlpool effect in the fluid, which is used in the cleaning and disinfecting cycle, as explained further below. Also shown with base portion 2 are an electronic control unit 21 for the system, a power supply contact prong 22 for insertion in the port opening 13 and establishing electrical contact with the contact element 12 for the UV lamp 10 when the upper housing part is fitted onto the base portion 2 during use, and a mounting part 23 for securing the other end of the pedal spring 20b.

A lens holder 14 is provided for holding contact lenses immersed in the cleaning fluid in the cleaning and disinfecting chamber 15-16. The lens holder has a pair of lower lens holder portions 14a, 14b carried from an upper bracket 14c. The upper bracket 14c extends to a pair of arms 14d, 14e which are mounted onto respective sides of the base portion 2 of the housing to suspend the lens holder portions in the fluid.

Figure 3:
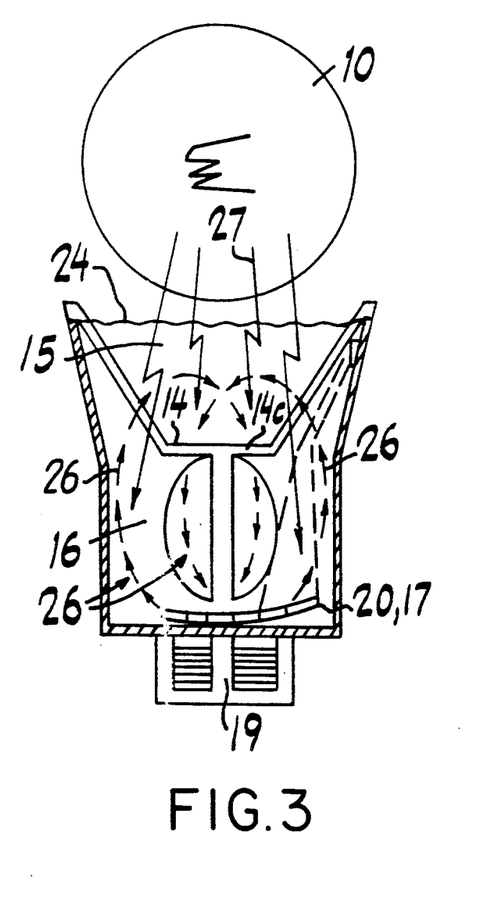
FIG. 3 is a schematic diagram illustrating the cleaning and disinfecting functions of the contact lens cleaning system.

FIG. 3 shows the function of the various components of the cleaning system during use. A given volume of fluid 24 is filled in the cleaning and disinfecting chamber 15-16. The contact lenses are placed in the holder portions of the lens holder 14. Magnetic coupling of the fluctuating magnetic flux provided by the driving transformer 19 causes the magnetic-disk containing pedal 17, 20 to oscillate, creating whirlpool waves 26 in the chamber. The turbulent waves 26 rinses through, cleans, and dislodges particles, films, and other deposits from the lenses. The deposits are carried by the whirlpool waves 26 to the upper, disinfecting chamber 15, above the upper bracket 14c of the lens holder where they are disinfected by the UV radiation 27 from the UV lamp 10. The disinfected deposits tend to settle on the upper bracket 14c where they are collected and later removed. The upper bracket portion 14c is interposed between the UV lamp and the lens holder portions to block the UV rays from directly irradiating on the contact lenses. The energy of the UV rays decreases exponentially with distance travelled through the fluid, so that the energy of the rays becomes completely dispersed at the bottom of the chamber. Thus, UV degradation of the lens polymer material is prevented.

Figure 5:
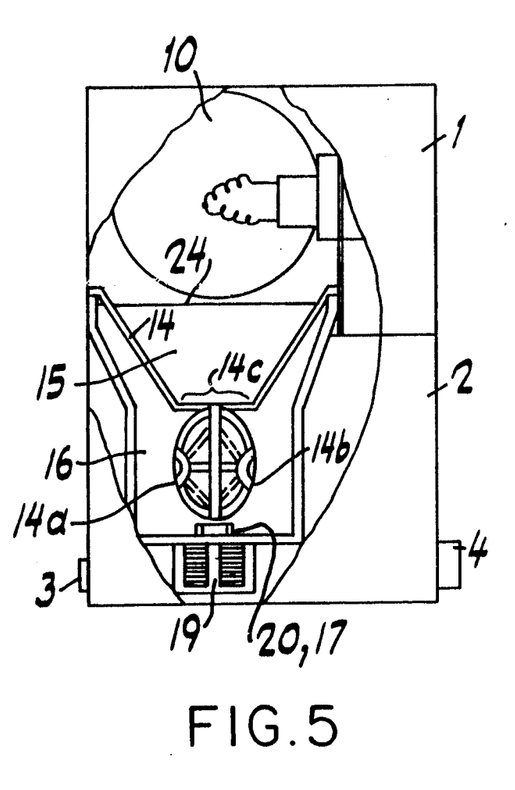
FIG. 5 is a side schematic view showing the arrangement of the components of the cleaning system during use.

In FIG. 4, the magnetic disk 17 is shown embedded or encapsulated in the plastic pedal 20a. The plastic encapsulation protects the magnetic disk from corrosion from the saline solution. The stainless steel spring 20b is also corrosion resistant. As an alternative, a magnetic rotor may be used instead of the springmounted pedal. The rotor is driven in rotation by a rotating magnetic flux generated by the driving transformer 19. FIG. 5 shows the arrangement of the components when the upper housing portion 1 is fitted onto the lower base portion 2.

Figure 6A:
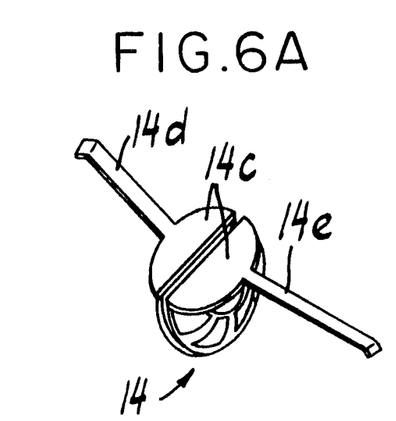
FIG. 6A-B is a detailed view of a lens holder for use in the cleaning system.
Figure 6B:
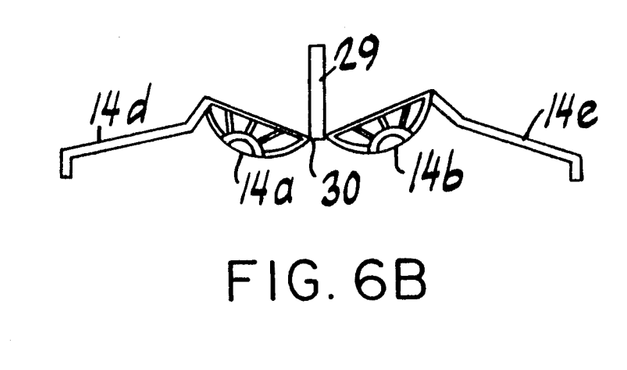

In FIG. 6A-B, the lens holder is shown in more detail, wherein the upper bracket 14c consists of left and right hemispherical parts which shade and protect the lenses from direct exposure to the UV light. Contact lens plastic polymers degrade from long accumulated exposure to UV light. The shading and protection of the lenses from direct UV radiation thus provides an important advantage over conventional UV disinfecting units. The parts of the upper bracket also serve as a roof for collecting deposits floated to and disinfected in the upper chamber, and prevent them from resettling on the lenses. The left and right hemispherical parts of the lens holder can pivot along a connecting leaf 30 to open outwardly so that the respective lenses can be placed in the lens holding portions 14a, 14b. The holder can be injection nolded as a single piece without a hinge, in order to avoid the use of abutting corners or edges which can retain microorganisms. A divider 29 separates the two lens holding portions and is provided with snaps or detents to snap together with one or both of the lens holding portions.

Figure 7:
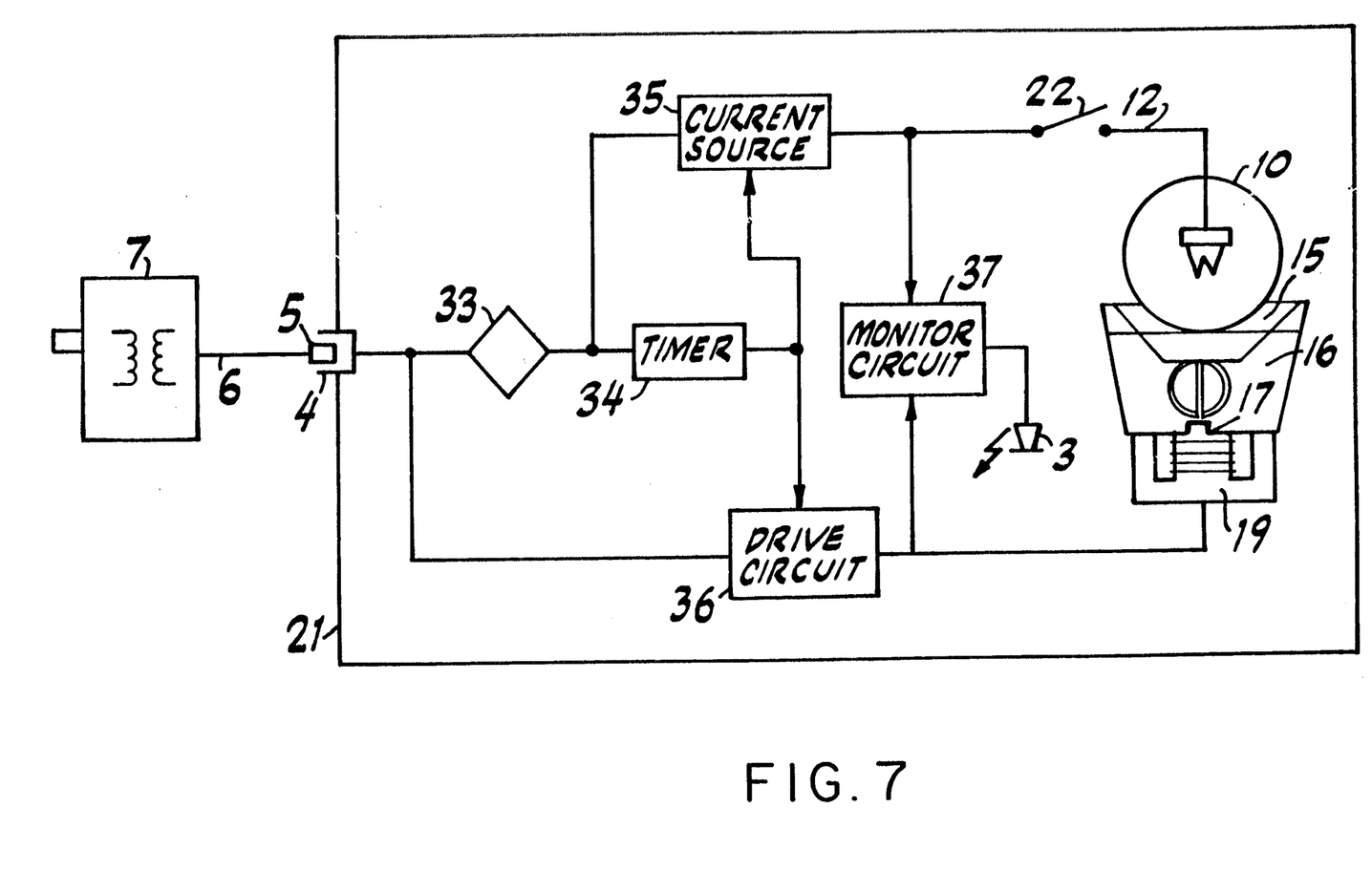
FIG. 7 is a schematic diagram of an electronic control unit for the cleaning system.

FIG. 7 is a circuit diagram for the electronic control of the cleaning system. The step-down power transformer 7 provides a low voltage power of about 14 volts AC, via cord 6, plug 5, and receptacle 4, to the electronic control circuit 21, which is shown embodied on a circuit board carried in the lower base portion 2 of the housing. The isolation, wall-plugged transformer 7 can operate selectively from a 120 or 220 volt power supply. Separation of the power transformer from the cleaning unit itself removes the danger of hazardous electrical shock from the unit which contains the saline solution. Also, the low stepped-down voltage is preferred for safe operation and a long service life of the components.

The low voltage AC input is converted to a stable DC voltage by a full bridge rectifier 33 for the control circuits and UV lamp. The DC voltage is supplied to a timer 34 which times the ON-cycle of a driver current source 35, which stabilizes and controls the current provided to the disinfecting UV lamp 10, and a driving circuit 36 which controls the supply of AC current to the driving transformer 19 for the whirlpool-generating pedal or rotor 17. A monitoring circuit 37 monitors both the driver current provided to the UV lamp and the voltage supplied to the whirlpool-driving transformer 19, and indicates proper operation through the indicator light 3 which may be a light-emitting diode. The monitoring circuit 37 may consists of current and voltage comparators, which are common electronic components that can be obtained commercially. Should either one of these cleaning and disinfecting circuits fail or shut down, through detection of an improper or zero current or voltage, circuit, the indicator light will not be lit, and the user will have a visual indication that the cleaning cycle has ended or that the unit is not functioning properly.

The electronic control of the operation of the cleaning system will now be described. The user first places the contact lenses in the lens holding portions 14a, 14b of the lens holder 14 (without the need for any prior washing or scrubbing with soap), and mounts the lens holder in the cleaning/disinfecting chamber 15-16 of the base portion 2. Saline solution is filled in the chamber to a designated fill line, for example, a volume of about 20 ml. is sufficient for the dimensions of the unit indicated. The upper housing portion 1 is then fitted onto the base portion 2, with the contact prong 22 being inserted in the port opening 13 and positioned in electrical contact with the UV lamp contact 12. Requiring placement of the upper housing on the base portion before electrical contact for the UV lamp can be made provides a switch interlock safety feature for the system. This is indicated by the representation of a switch 22 and contact 12 in FIG. 7.

When the power cord plug 5 is inserted into the power supply receptacle 4, DC power is supplied to the timer circuit 34 which turns on the UV lamp driving circuit 35 and the whirlpool driving circuit 36 at the same time. The indicator light 3 is thus turned on. The cleaning and disinfecting circuits are operated together for a given cleaning cycle, for example, 30 minutes. The timer 34 then times out, and shuts off the UV lamp current source 35 and the whirlpool driving circuit 36 either at the same time or in a selected phased sequence. When the cleaning and disinfecting circuits have been shut down, the indicator light 3 is turned off.

The disinfecting lamp is part of the upper housing which must be plugged onto the lower base to start the cleaning cycle. Once the lamp is connected, and power is supplied, the timer is triggered to turn on the system for a 20-30 minute cleaning cycle. At the end of the cycle, the timer shuts the system components off and remains in a standby mode until the upper housing is removed and replugged.

The UV lamp is a common germicidal component which may be obtained commercially. They have been used in the pharmaceutical industry for a long time, and are well known as a disinfection measure for killing bacteria, viruses, mold spores, and other microorganisms. The standard germicidal UV lamp is typically a mercury vapor lamp (e.g., G4S11 unit) which will generate light of short wavelengths with a peak at about 253.7 nanometers, which is the wavelength found to be most effective in killing and disinfecting microorganisms. The duration and intensity of UV radiation determines the effectiveness for disinfection. High intensity for a short period of time, or lower intensity over a long duration, is needed for lethal action on bacteria. UV lamp energy is measured in microwatts per square centimeters ($\mu w/cm^2$). The worst case organism is fungus which requires about 400,000 $\mu w/cm^2$. To obtain this level of energy with a lamp of standard intensity, a longer exposure duration is needed. For example, if the average energy of a standard UV lamp at a distance of one inch is 1000 $\mu w/cm^2$, then the exposure time for worst case fungus should be 400 seconds, which is equal to 6.6 minutes. For complete cleaning and disinfection of contact lenses, it is found that a disinfecting exposure cycle of about 20-30 minutes is sufficient.

Figure 8:
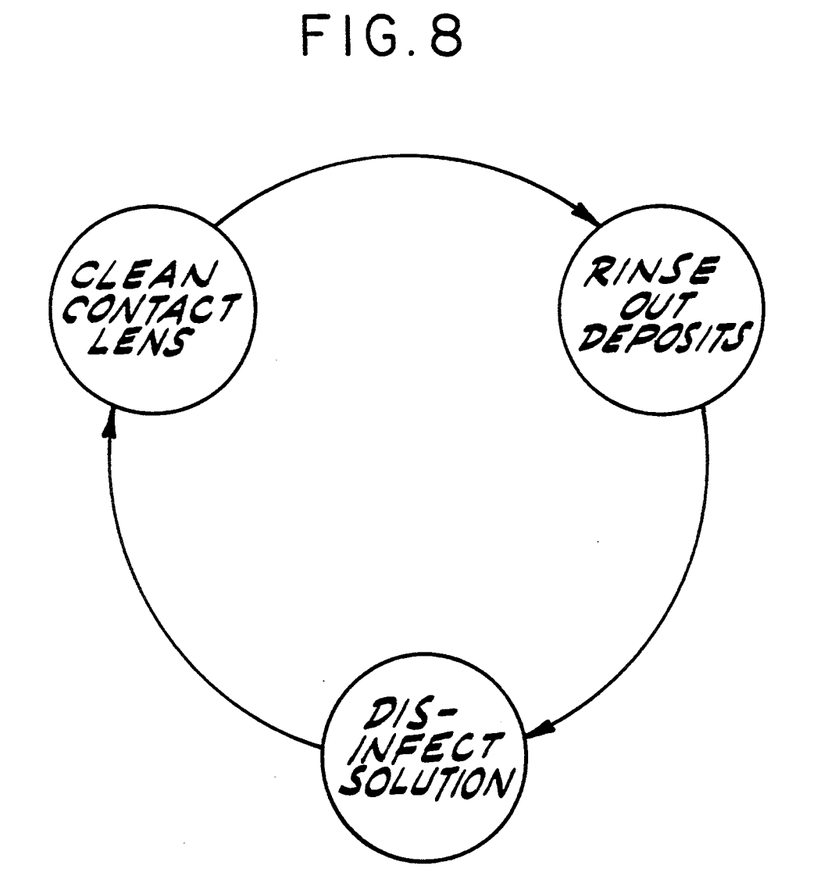
FIG. 8 illustrates the steps of the cleaning system cycle.

The lower cleaning chamber 16 is designed to minimize reflections of UV rays toward the contact lenses in the lens holder. The whirlpool action and water pressure in the lower chamber drives the deposits and organisms dislodged by the whirlpool action to the upper disinfecting chamber 15 where they are disinfected by UV rays from the UV lamp at close range. The cleaning solution, as it is disinfected in the upper chamber, returns by the whirlpool action to the lower chamber for further rinsing and flushing of the contact lenses during the 20-30 minute cleaning cycle. The integration of these steps in the cleaning cycle is illustrated in FIG. 8.

The magnetic pedal 17 can be driven at a low oscillation speed of about 50-120 cycles/second to generate a suitable whirlpool for sub-sonic turbulence cleaning. This sub-sonic operation is found to be advantageous over ultra-sonic methods which can dissolve deposits by cavitation but does not dislodge them from the surface of the lens so that they can be removed and UV disinfected at a location remote from the lenses. In contrast, the sub-sonic whirlpool rinsing and flushing of the present invention produces excellent cleaning of the lens surface, without generating any heat or cavitation effects in the solution, and removes the dislodged deposits to the upper chamber for UV disinfection. The whirlpool pedal is designed to stir the solution by oscillating at a steady amplitude. It is tethered by the flexible spring to the wall of the container in order to prevent it from wandering (as distinct from the common form of magnetic stirrer used in this industry). The driving transformer for the pedal is located outside the chamber beneath the bottom wall, and may be a common type of audio transformer with an open core.

The system of the present invention thus integrates effective cleaning and disinfecting functions, and avoids entirely the expense, inconvenience, time consumption, physical degradation of the lenses, and risk of eye irritation and infection of the conventional lens cleaning methods. The compact single unit design, short cleaning cycle, and safety features, such as low voltage power supply and switch interlock for the UV lamp, make the system highly convenient and safe to use, and ideal for portable or travelling use. No outside intervention or prior manual rubbing or rinsing is required. The system can clean and disinfect all types of contact lenses, i.e., hard, soft, etc., effectively in a single, short cleaning cycle, and with only the use of a small volume of unpreserved saline solution.

Although the invention has been described with reference to certain preferred embodiments, it will be appreciated that many variations and modifications may be made consistent with the broad principles of the invention. It is intended that the preferred embodiments and all of such variations and modifications be included within the scope and spirit of the invention, as defined in the following claims.

I claim:

1. A contact lens cleaning and disinfecting system comprising:
   an enclosed housing having a chamber for holding a volume of fluid therein;
   a source of ultraviolet (UV) radiation mounted at an upper portion of the chamber above the volume of fluid;
   a lens holder having lens holder portions for holding respective contact lenses in the chamber immersed in the volume of fluid;
   a turbulence mechanism for inducing turbulence in the volume of fluid with sufficient force to dislodge particles, films, and other deposits from the lenses into the fluid; and
   an electronic control unit for operating the source of ultraviolet radiation to disinfect the dislodged particles, films, and other deposits in the fluid.

2. A contact lens cleaning and disinfecting system according to claim 1, wherein said housing is formed with an upper housing part holding the UV source, and a lower base portion containing the fluid-holding chamber.

3. A contact lens cleaning and disinfecting system according to claim 2, wherein said lower base portion contains said electronic control circuit and has a contact element for supplying power to the UV source, and said upper housing portion has a contact element electrically connected to the UV source, said contact element of the lower base portion being placed into electrical contact with the contact element of the upper housing portion when the upper housing portion is fitted onto the lower base portion for operation of a cleaning/disinfecting cycle, whereby accidental operation and irradiation by the UV source is prevented.

4. A contact lens cleaning and disinfecting system according to claim 3, wherein said contact element of the lower base portion is a prong contact projecting therefrom, and said upper housing portion has a port opening for receiving the prong contact of the lower base portion therein and placing it into electrical contact with the contact element of the upper housing portion when the upper housing portion is fitted onto the lower base portion.

5. A contact lens cleaning and disinfecting system according to claim 2, wherein said electronic control circuit is contained in the lower base portion, and said lower base portion has a low-voltage power receptacle for receiving a plug end of a power cord from an isolation power transformer unit which is wall-plugged with a standard power supply line.

6. A contact lens cleaning and disinfecting system according to claim 1, wherein said chamber has a lower cleaning portion and an upper disinfecting portion, and said lens holder has a pair of lower lens holder portions carried by an upper bracket which is mounted in the housing so as to suspend the lens holder portions in the lower cleaning portion of the chamber.

7. A contact lens cleaning and disinfecting system according to claim 6, wherein said upper bracket portion is immersed in the fluid between the upper and lower portions of the chamber and is interposed between the UV source and the lens holder portions to prevent UV rays from directly irradiating on the contact lenses, thereby preventing UV degradation of the lens polymer material.

8. A contact lens cleaning and disinfecting system according to claim 7, wherein said lens holder is formed with left and right holding portions and a divider interposed between them, said holding portions being arranged to open apart for placement of respective contact lenses therein, and to close together for retaining the lenses therein and for forming said upper bracket portion for shading and protection of the lenses from UV radiation.

9. A contact lens cleaning and disinfecting system according to claim 8, wherein said lens holder is formed as a single injection-molded piece.

10. A contact lens cleaning and disinfecting system according to claim 7, wherein said turbulence mechanism is operated to create a whirlpool in the fluid sufficient to dislodge particles, films, and other deposits from the lenses and carry the dislodged deposits to the upper portion of the chamber above the upper bracket portion of the lens holder where they can be disinfected by the UV radiation.

11. A contact lens cleaning and disinfecting system according to claim 1, wherein said turbulence mechanism includes a pedal having a magnetic element which is positioned at a central position toward a bottom wall of the chamber and is driven by a magnetic flux generator located beneath the bottom wall.

12. A contact lens cleaning and disinfecting system according to claim 11, wherein said pedal has one end tethered to a flexible spring element fixed to one side of the chamber to prevent the pedal from wandering around the chamber.

13. A contact lens cleaning and disinfecting system according to claim 11, wherein said magnetic flux generator is operated to oscillate the pedal in steady oscillation cycles that generate a whirlpool which swirls in and around the lens holder portions.

14. A contact lens cleaning and disinfecting system according to claim 13, wherein said magnetic flux generator is operated to oscillate the pedal in the range of 50-120 oscillation cycles per second.

15. A contact lens cleaning and disinfecting system according to claim 1, wherein said electronic control unit includes a first driver circuit for said UV source, a second driver circuit for said turbulence mechanism, and a timer circuit for operating said first and second driver circuits in an ON-cycle for a predetermined period of time.

16. A contact lens cleaning and disinfecting system according to claim 15, wherein said electronic control unit includes a monitoring circuit for monitoring the ON-cycle of operation of the said first and second driver circuits, and an indicator light connected to said monitoring circuit for providing a visual indication of proper operation of said UV source and turbulence mechanism during the ON-cycle.

17. A contact lens cleaning and disinfecting system according to claim 1, wherein the fluid used in said chamber is non-preserved saline solution which does not contain any chemical irritants.

18. A contact lens cleaning and disinfecting system according to claim 1, wherein said electronic control circuit operates the disinfecting UV source and the cleaning turbulence mechanism for a cleaning/disinfecting cycle in the range of 20-30 minutes.

19. A contact lens cleaning and disinfecting system according to claim 1, wherein said electronic control circuit operates the disinfecting UV source and the cleaning turbulence mechanism for a cleaning/disinfecting cycle without any heating of the contact lenses.

20. A contact lens cleaning and disinfecting system according to claim 1, wherein said UV source is a germidical UV lamp which generates UV with a peak at about 253.7 nanometers.

* * * * *